United States Patent
Ge et al.

(10) Patent No.: US 10,472,573 B2
(45) Date of Patent: *Nov. 12, 2019

(54) METHOD FOR DIRECT PRODUCTION OF GASOLINE-RANGE HYDROCARBONS FROM CARBON DIOXIDE HYDROGENATION

(71) Applicant: DALIAN INSTITUTE OF CHEMICAL PHYSICS, CHINESE ACADEMY OF SCIENCES, Dalian (CN)

(72) Inventors: Qingjie Ge, Dalian (CN); Jian Wei, Dalian (CN); Hengyong Xu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/069,262

(22) PCT Filed: Jul. 31, 2017

(86) PCT No.: PCT/CN2017/095133
§ 371 (c)(1),
(2) Date: Jul. 11, 2018

(87) PCT Pub. No.: WO2018/049938
PCT Pub. Date: Mar. 22, 2018

(65) Prior Publication Data
US 2019/0016964 A1 Jan. 17, 2019

(30) Foreign Application Priority Data

Sep. 19, 2016 (CN) .......................... 2016 1 0830043

(51) Int. Cl.
| | | |
|---|---|---|
| C10G 2/00 | (2006.01) | |
| B01J 29/46 | (2006.01) | |
| B01J 37/00 | (2006.01) | |
| B01J 37/02 | (2006.01) | |
| B01J 37/03 | (2006.01) | |
| B01J 37/04 | (2006.01) | |
| B01J 37/06 | (2006.01) | |
| B01J 37/08 | (2006.01) | |

(52) U.S. Cl.
CPC .............. *C10G 2/50* (2013.01); *B01J 29/46* (2013.01); *B01J 37/009* (2013.01); *B01J 37/0236* (2013.01); *B01J 37/031* (2013.01); *B01J 37/04* (2013.01); *B01J 37/06* (2013.01); *B01J 37/08* (2013.01); *C10G 2300/70* (2013.01); *C10G 2400/02* (2013.01)

(58) Field of Classification Search
CPC ....................................................... C10G 2/50
See application file for complete search history.

(56) References Cited

U.S. PATENT DOCUMENTS 5,865,988 A    2/1999    Collins et al.

FOREIGN PATENT DOCUMENTS

| CN | 1127240 | A | 7/1996 | |
|---|---|---|---|---|
| CN | 101352689 | A | 1/2009 | |
| CN | 102091618 | A | 6/2011 | |
| CN | 102941098 | A | 2/2013 | |
| CN | 104117380 | A | 10/2014 | |
| CN | 104368378 | A | 2/2015 | |
| CN | 104368378 | A | 2/2015 | |
| CN | 104496743 | A | 4/2015 | |
| CN | 104624194 | A | 5/2015 | |
| CN | 105289710 | A | 2/2016 | |
| DE | 102013022290 | A1 * | 3/2015 | ............. B01J 37/04 |
| WO | 2012135089 | A1 | 10/2012 | |

OTHER PUBLICATIONS

Fujiwara, M. et al. "Change of catalytic properties of Fe—ZnO/zeolite composite catalyst in the hydrogenation of carbon dioxide" Applied Catalysis A: General 154 (1997) 87-101 (Year: 1997).*
DE-102013022290-A1, translation, Mar. 26, 2015, pp. 1-16 (Year: 2015).*
("Main sources of carbon dioxide emissions" Jun. 3, 2016 (Year: 2016).*
("Gasoline" from Chemical and Physical Information, 2019 (Year: 2019).*
Wei, J. et al. "Directly converting CO2 into a gasoline fuel" Nature Communication, Published May 2, 2017 (Year: 2017).*
Riedel, T. et al. "Comparative study of Fischer-Tropsch synthesis with H2/CO and H2/CO2 syngas using Fe- and CO-based catalysts" Applied Catalysis A: General 186 (1999) 201-213 (Year: 1999).*
Yisheng Tan et al., "Syntheses of Isobutane and Branched Higher Hydrocarbons from Carbon Dioxide and Hydrogen over Composite Catalysts", Ind. Eng. Chem. Res. 1999, 38, 3225-3229.

(Continued)

*Primary Examiner* — Medhanit W Bahta
(74) *Attorney, Agent, or Firm* — Enshan Hong; VLP Law Group LLP

(57) ABSTRACT

A method for carbon dioxide direct hydrogenation to gasoline-range hydrocarbons is provided in this invention. Under the reaction conditions of 250-450° C., 0.01-10.0 MPa, 500-50000 mL/(h·$g_{cat}$) of feedstocks, 0.5-8 molar ratio of $H_2$ to $CO_2$, the mixture of carbon dioxide and hydrogen may be directly converted to gasoline-range hydrocarbons over a multifunctional hybrid catalyst. The multifunctional hybrid catalyst comprises: iron-based catalyst for carbon dioxide hydrogenation as the first component, one, two or more of zeolites optionally modified by metal as the second component. In this method, a per-pass conversion of $CO_2$ may achieve more than 33%, the methane selectivity in the hydrocarbon products is less than 8%, the selectivity of gasoline-range hydrocarbons with carbon numbers from 5 to 11 in the hydrocarbon products is more than 70%. The obtained gasoline-range hydrocarbons exhibit high octane number due to its composition comprising isoparaffins and aromatics as the major components.

18 Claims, No Drawings

(56) References Cited

OTHER PUBLICATIONS

Masahiro Fujiwaraa et al., "CO2 hydrogenation for C2+ hydrocarbon synthesis over composite catalyst using surface modified HB zeolite", Applied Catalysis B: Environmental 179 (2015) 37-43.
Y. Tan et al. Ind. Eng. Chem. Res. 38 (1999) 3225-3229.
M. Fujiwara et al. Appl. Catal. B: Environ 179 (2015) 37-43.

\* cited by examiner

METHOD FOR DIRECT PRODUCTION OF GASOLINE-RANGE HYDROCARBONS FROM CARBON DIOXIDE HYDROGENATION

RELATED APPLICATIONS

This is a U.S. national stage of international application No. PCT/CN2017/095133 filed on Jul. 31, 2017, which claims priority from China Patent Application No. 201610830043.1 filed on Sep. 19, 2016, the entire content of which is incorporated herein as reference.

TECHNICAL FIELD

This invention relates to a method for $CO_2$ hydrogenation to produce gasoline, in particular, a method for $CO_2$ hydrogenation to produce high quality gasoline.

BACKGROUND OF THIS INVENTION

Gasoline, $C_{5-11}$ hydrocarbons, is a kind of necessary transportation fuels for the development of modern society. At present, gasoline is produced mainly from petroleum by the process of direct distillation and catalytic cracking of crude oil, however, due to the limitation of petroleum resource reserve, developing the gasoline production technology from nonpetroleum resources is already becoming research targets of lots of countries. $CO_2$, as the cheapest and most abundant resources of $C_1$ compounds, has a plentiful of storage on the earth. Along with the continuous development of human society and the rapid increase of consumption of fossil energy resources, $CO_2$ concentration in atmosphere increases sharply, which not only intensifies the greenhouse effect, but also results in the huge waste of carbon resources. The $CO_2$ derived from industrial waste gases or captured from atmosphere and the hydrogen derived from renewable energy sources could be used as feedstocks for the catalytic conversion of $CO_2$ to liquid hydrocarbons, such process has the significance to solve not only the climate change but also energy crisis, that peoples encountered in modern society.

The research results indicate that, the hydrocarbons synthesis from $CO_2$ hydrogenation generally includes the next two steps: first, $CO_2$ react with $H_2$ to form CO via RWGS (Reverse water gas shift) reaction, and then, CO conversion to hydrocarbons via Fischer-Tropsch synthesis (F-T synthesis) reaction. For the traditional F-T synthesis of CO hydrogenation to hydrocarbons, the product selectivity follows the rules of Anderson-Schulz-Flory (ASF) distribution. According to ASF rules of hydrocarbon distribution, the content of gasoline hydrocarbons ($C_{5-11}$ hydrocarbons) in hydrocarbon products is not more than 45%. Different from that in CO hydrogenation process, there exists a low C/H ratio on the surface of catalyst in $CO_2$ hydrogenation process due to the slow adsorption of $CO_2$ on the catalyst surface. Such phenomena in $CO_2$ hydrogenation is beneficial to hydrogenation of adsorbed species and decrease of probability for product chain growth, and thus selectivity to methane is further raised while the formation of long chain hydrocarbons becomes more difficult. Therefore, about the present literatures' studies on $CO_2$ hydrogenation, the target products concentrate on small molecular weight compounds such as methanol (e.g. CN201110006073.8), dimethyl ether (e.g. CN201410495290.1), methane (e.g. CN201210444697.2), and light olefins (e.g. CN201510102620.0), a few studies on long chain hydrocarbon synthesis from $CO_2$ hydrogenation. The literature (Y Tan et al. Ind. Eng. Chem. Res. 38 (1999) 3225-3229) reported that 52% of $C_{5+}$ hydrocarbons in total hydrocarbons could be obtained at 19.5% of $CO_2$ conversion, however, 57.4% of selectivity to byproduct CO exist in this process, the yield of $C_{5+}$ hydrocarbons is very low. M. Fujiwara et al. (Appl. Catal. B: Environ 179 (2015) 37-43) recently found that over the hybrid catalysts, comprised of Cu—Zn—Al methanol synthesis catalyst and modified HB zeolite, $C_{2+}$ hydrocarbons could be obtained from $CO_2$ hydrogenation, however, selectivity to byproduct CO is higher than 50%.

Altogether, although some progresses have been made in the studies on $CO_2$ hydrogenation to gasoline-range hydrocarbons, selectivity to gasoline-range hydrocarbons, the target products, is still low, and selectivities to CO and $CH_4$ are still high, which is far away from the requirement of practical use. So, the urgent task for $CO_2$ conversion to gasoline is to find a high efficient process for $CO_2$ hydrogenation to gasoline with high $CO_2$ conversion and high selectivity to gasoline.

SUMMARY OF THE INVENTION

A method for $CO_2$ hydrogenation to gasoline is provided in this invention to solve the following problems existed in the literature related studies: low selectivity to gasoline-range hydrocarbons, target product, high selectivities to CO and methane, byproducts, and low use ratio of $CO_2$.

In this invention, a method for $CO_2$ direct hydrogenation to gasoline-range hydrocarbons is provided, whose characteristics include: feed gases comprising carbon dioxide and hydrogen, could be directly converted to gasoline-range hydrocarbons with high quality over a multifunctional hybrid catalyst. The multifunctional hybrid catalyst comprises the following components: iron-based catalyst for carbon dioxide hydrogenation as the first component, one, two or more of zeolites modified or unmodified by metal as the second component. The mass ratio of the first component to the second component is 1:10 to 10:1, with the optimal value being 1:3 to 3:1. The resultant high-quality gasoline exhibits the following characteristics: no contaminants of sulfur- or nitrogen-compounds, low olefin content, high isoparaffin content, and high octane value.

In this invention, the reaction conditions of $CO_2$ hydrogenation to gasoline-range hydrocarbons are: 250-450° C., 0.01-10.0 MPa, 500-50000 mL/(h·$g_{cat}$) of feedstocks, 0.5-8.0 molar ratio of $H_2$ to $CO_2$ in feedstocks.

The main component of Fe-based catalysts for $CO_2$ hydrogenation is $Fe_3O_4$ with or without oxide promoters, the weight percent of oxide promoters in the catalyst composition is not more than 30%, or 0.5-10%. The oxide promoters comprise one or more metal oxides selected from the oxide group comprising of sodium oxide, potassium oxide, manganese oxides, copper oxide, zirconium oxide, vanadium oxides, zinc oxide, cerium oxides.

The zeolite is ZSM-5, ZSM-22, ZSM-23, Y, Beta, MOR, MCM-22 or a mixture thereof; wherein the zeolite is preferably ZSM-5 with 20-350 molar ratio of $SiO_2$ to $Al_2O_3$, and/or, MCM-22 with 20-200 molar ratio of $SiO_2$ to $Al_2O_3$. Wherein the metal in the metal-modified zeolite is Mo, Zn, Rh, Ru, Ga, Cr, Co, Ni, Na, Cu, Pd, Pt, La or a mixture thereof; The weight percent of metal elements in the metal-modified zeolite is 0.1-20% or 0.5-10%.

Fe-based catalyst components for $CO_2$ hydrogenation may be obtained by one of the following three preparation methods:

A. One-pot synthesis method, comprising the following procedures:

(1) According to the catalyst composition ratio, soluble Fe(II) salt and Fe(III) salt were mixed and dissolved to form salt solution-I; or soluble Fe(II) salt, Fe(III) salt, and soluble promoter salt were mixed and dissolved to form salt solution-II. Wherein the salt solution-I or salt solution-II, the concentration of Fe(III) is 0.05-1 mol/L, HCl solution with 5-12.1 mol/L HCl concentration was added into salt solution-I and solution-II for adjusting the pH value to 0-3. The molar ratio of Fe(III) to Fe(II) in salt solutions is 2:(1~3); Soluble Fe(II) salt and Fe(II) salt is the salt compound that could be dissolved into water, which includes chloride, nitrate, acetates, or a mixture thereof. Promoter salt is the salt compounds that could be dissolved into water, which includes chloride, nitrate, acetates, or a mixture thereof.

(2) The alkali solution was added dropwise into solution I and solution II, obtained from procedure (1), for adjusting pH value of solutions from 0-3 to 9-12. After finishing the titration, the titrated solution was aged for 1-5 hours. The above alkali solution is the alkaline solution that could adjust the pH value of salt solution, it preferably is NaOH, KOH, $Na_2CO_3$, $NaHCO_3$, $K_2CO_3$, $KHCO_3$, $Na_2C_2O_4$, $K_2C_2O_4$, RCOONa, RCOOK, $NH_3.H_2O$ or a mixture thereof. The concentration of alkali solution is 0.1-10 mol/L; Among RCOOK and RCOONa, R is an organic group, comprising alkyl group, alkenyl group and aryl group, or preferably be methyl, ethyl, and phenyl group.

(3) After reaction in (2), the precipitates are separated from solutions in (2) by magnetic adsorption, centrifugation or suction filtration method, and fully washed with distilled water, dried, calcined/not calcined at 200-600° C. for 2-10 hours to obtain Fe-based catalysts.

B. One-pot synthesis method, comprising the following procedures:

(1) According to the catalyst composition ratio, soluble Fe(II) salt and Fe(III) salt were mixed and dissolved to form salt solution, wherein the salt solution, the concentration of Fe(III) is 0.05-1 mol/L, HCl solution with 5-12.1 mol/L HCl concentration was added into salt solution for adjusting the pH value to 0-3. The molar ratio of Fe(III) to Fe(II) in salt solutions is 2:(1~3);

(2) The alkali solution containing Na or K described in method A was added dropwise into the salt solution obtained from procedure (1), for adjusting pH value of solutions from 0-3 to 9-12. After finishing the titration, the titrated solution was aged for 1-5 hours.

(3) After reaction in (2), the precipitates were separated from solutions in (2) by magnetic adsorption, centrifugation or suction filtration method, and fully washed with distilled water, which could control the content of residue Na or K by controlling the times and water usage of washing. And then the washed precipitates were dried, calcined/not calcined at 200-600° C. for 2-10 hours to obtain Fe-based catalysts with promoter Na or K.

C. First synthesis of $Fe_3O_4$ by coprecipitation method, and then addition of promoters by impregnation methods. Such preparation methods comprise the following procedures:

(1) According to the catalyst composition ratio, soluble Fe(II) salt and Fe(III) salt were mixed and dissolved to form salt solution, wherein the salt solution, the concentration of Fe(III) is 0.05-1 mol/L, HCl solution with 5-12.1 mol/L HCl concentration was added into salt solution for adjusting the pH value to 0-3. The molar ratio of Fe(III) to Fe(II) in salt solutions is 2:(1~3);

(2) The alkali solution described in A method was added dropwise into the solution obtained from procedure (1), for adjusting pH value of solutions from 0-3 to 9-12. After finishing the titration, the titrated solution was aged for 1-5 hours.

(3) After reaction in (2), the precipitates were separated from solutions in (2) by magnetic adsorption, centrifugation or suction filtration method, and fully washed with distilled water, dried to form active composition $Fe_3O_4$.

(4) Catalyst synthesis from the combination of active composition $Fe_3O_4$ and promoter salt, the detailed procedures are: according to the needed promoter content, the mass of promoter salt was calculated, and then the solution of promoter salt was prepared, and $Fe_3O_4$ as obtained in (3) was impregnated with promoter salt solution by equivalent-volume impregnation methods, after stirring, stewing, drying, calcination at 200-600° C. for 2-10 h, the iron-based catalyst with promoter was obtained.

The zeolite modification could be carried out according to one of the following methods for supporting metal component:

(1) equivalent-volume impregnation method, the detail procedures are as follows: according to the needed metal content, the theoretical mass of metal salt was calculated, and then the solution of metal salt was prepared. The metal salt could be one, two or more of the following salts: nitrate, chloride, bromide, acetate, acetylacetonate, citrate, oxalate. The zeolite to be modified was impregnated with the as-prepared salt solution by equivalent-volume impregnation methods, after stirring, stewing, drying, calcination at 300-700° C. for 2-10 h, the modified zeolite was obtained.

(2) ion-exchanged method, the detail procedures are as follows: according to the needed metal content, the theoretical mass of metal salt was calculated, and then the solution of metal salt was prepared. The metal salt could be one, two or more of the following salts: nitrate, chloride, bromide, acetate, acetylacetonate, citrate, oxalate. The zeolite to be modified was impregnated with the as-prepared salt solution by equivalent-volume impregnation methods, after stirring, stewing, drying, calcination at 300-700° C. for 2-10 h, the modified zeolite was obtained. The zeolite to be modified was mixed with the as-prepared metal salt solution at 1:(10-200) of mass ratio of solid to solution, and ion-exchanged for 2-24 h, after water washing, drying, calcination at 300-700° C. for 2-10 h, the metal-modified zeolite was obtained.

The two components of multifunctional catalysts could be mixed according to any one of the following three methods, preferably according to granule mixing method or multilayer catalyst packing method.

(1) Powder mixing method: the powder of iron-based catalyst and zeolite was grounded mixing at the required mass ratio of iron-catalyst to zeolite, pelleted, crushed, and sieved to form multifunctional catalyst.

(2) Granule mixing method: the iron-based catalyst powder and zeolite powder was pelleted, crushed, and sieved, respectively. The sieved granules of iron-based catalysts and zeolites were mixed homogeneously at the required mass ratio of iron-catalyst to zeolite to form multifunctional catalyst.

(3) Multilayer catalyst packing method: catalysts was packed into the reactor according to the sequences of iron-based catalyst layer, and zeolite layer, among which iron-based catalyst layer is near to the feedstock inlet and zeolite layer is far to the feedstock inlet. Between iron-based catalyst layer and zeolite layer, there is or is not an isolated layer composed of inert materials, the mass ratio of the isolated layer to multifunctional catalyst is 0.01-10.

The performances of catalysts for $CO_2$ hydrogenation to gasoline-range hydrocarbons were evaluated as follows: Put the prepared hybrid multifunctional catalysts into the constant temperature zone of fixed-bed reactor, then reduce the catalyst for 2-12 hours in $H_2$ atmosphere at 300-400° C. and 10-50 mL/min of $H_2$ flow rate. After finishing reduction of catalyst, adjust the temperature to reaction temperature and switch the reducing gas to reaction feedstock to begin reaction. The products were introduced to gas chromatography in gaseous state for on-line analysis, among of which, CO, $N_2$, $CH_4$ and $CO_2$ were detected by TCD (thermal conductive detector) and hydrocarbons were detected by FID (flame ionization detector).

This invention could be applied to the gases containing carbon dioxide, the said gases means the gases containing carbon dioxide, the gases could be industrial waste gases, automobile exhaust, coal combustion exhaust, and carbon dioxide in atmosphere or seawater.

This invention could show the following characters:

(1) Catalyst: simple preparation method, starting material cheap and easy to get, high mechanical strength, high stability, suitable for applying in fixed-bed reactor, fluidized-bed reactor, and slurry-bed reactor, suitable for large-scale commercial process.

(2) Products: high quality clean gasoline fuel with sulfur-free, nitrogen-free, low content of olefins, high content of isoparaffins, the high-octane value gasoline product could be directly applied to fuel oil products, also be used as gasoline blending composition, or be used as the complement of other gasoline products.

(3) Reaction: one step synthesis of gasoline, simple reaction installation, short technological process, low equipment investment, low energy consumption.

(4) Utilization: this invention utilizes $CO_2$, a kind of greenhouse gas, as carbon resource, benefits to the recycling use of carbon resources, alleviates the dependence on fossil energy resources, also relieves the burden of environmental protection.

DESCRIPTION OF PREFERRED EMBODIMENTS

Technique details of this invention could be largely described by the following examples. It should be noted that the following examples are provided to illustrate, but not to limit this invention.

Example 1

31.62 g $FeCl_3 \cdot 6H_2O$ and 12.54 g $FeCl_2 \cdot 4H_2O$ were mixed and dissolved into 150 mL $H_2O$ to form iron salt solution, and then 5.1 mL of hydrochloric acid with 12.1 mol/L of HCl concentration were added into the said iron salt solution. After this, about 360 mL of 1.5 mol/L NaOH solution was added at a constant speed into the iron salt solution at stirring and 60° C., pH value of solution will be adjusted to 10.0 in about 1.5 h. After titration, the solution was continually stirring for 1 hour at 60° C., and then cooled to room temperature. After reaction, the precipitates were separated from the solution by magnetic adsorption, and washed once with 800 mL deioned water, and dried at 60° C. to obtained $Na/Fe_3O_4$ catalyst, which was further ground, pelleted, and sieved for use.

Zeolite pretreatment: zeolites were calcined at 500° C. for 4 hours, and then ground, pelleted and sieved for use. Here, zeolites includes zeolites from zeolite company of Nankai University, e.g. HY ($SiO_2/Al_2O_3=5$), HMCM-22 ($SiO_2/Al_2O_3=30$, HZSM-5 ($SiO_2/Al_2O_3=27$, 150, 300, respectively), zeolites from laboratory synthesis, e.g. HZSM-23 ($SiO_2/Al_2O_3=80$) and zeolites from Zeolyst company, e.g. HBEA ($SiO_2/Al_2O_3=25$), HMOR ($SiO_2/Al_2O_3=20$).

0.5 g said prepared $Na/Fe_3O_4$ granules and 0.5 g said HY or HBEA or HMOR or HZSM-23 or HMCM-22 or HZSM-5 zeolite granules were mixed homogenously for the catalyst evaluation in the fixed-bed reactor for $CO_2$ hydrogenation reaction. Reducing conditions: 1 atm, pure $H_2$ (25 mL/min), and 350° C. for 8 h. Reaction conditions: $H_2/CO_2=3.0$, 320° C., 3.0 MPa, and GHSV (Gas hourly space velocity): 4000 mL/(h·$g_{cat}$). Influences of different zeolites on the Fe—Na/Zeolite catalyst for $CO_2$ hydrogenation has been carried out, the results (Table 1) indicated that, hydrocarbon product distribution of $CO_2$ hydrogenation was affected by the channel and pore structure, the catalyst containing ZSM-5 exhibits excellent performances in the $CO_2$ hydrogenation due to the structure of HZSM-5: a three-dimensional porous network with two groups of interconnected 10-ring channels: ellipsoidal 5.3×5.6 Å and sinusoidal 5.1×5.5 Å and without cages at intersections. Gasoline-range hydrocarbon content in hydrocarbons varies with different kinds of zeolites: HZSM-5>HMCM-22>HZSM-23>HY>HBEA>HMOR. In addition, the product distribution of $CO_2$ hydrogenation is also influenced by the acidic strength of zeolites, HZSM-5 with $SiO_2/Al_2O_3=150$ and suitable acidic sites and strength, made the Na—$Fe_3O_4$/HZSM-5 catalyst exhibit the best $CO_2$ hydrogenation performance and highest selectivity to the gasoline-range hydrocarbons.

TABLE 1

Influences of zeolites on the FeNa/Zeolite hybrid catalysts for $CO_2$ hydrogenation

| Zeolite | Conv.* $CO_2$ (%) | Selec.* CO (%) | Hydrocarbon distribution (C-mol %) | | | | $O/P^a$ | $i\text{-}C_5/n\text{-}C_5^b$ |
| --- | --- | --- | --- | --- | --- | --- | --- | --- |
| | | | $CH_4$ | $C_2\text{~}C_4$ | $C_5\text{~}C_{11}$ | $C_{12+}$ | | |
| —$^c$ | 34.0 | 14.3 | 11.7 | 48.4 | 37.9 | 2.0 | 6.2 | 1.4 |
| HMOR | 35.0 | 12.0 | 9.8 | 47.2 | 42.8 | 0.2 | 4.5 | 1.2 |
| HBEA | 35.3 | 11.8 | 10.7 | 44.7 | 43.9 | 0.7 | 2.0 | 3.5 |
| HY | 34.1 | 13.7 | 10.0 | 40.5 | 47.9 | 1.6 | 1.2 | 4.1 |
| HZSM-23 | 33.7 | 14.7 | 10.6 | 37.8 | 51.0 | 0.6 | 3.2 | 1.1 |
| HMCM-22 | 34.8 | 13.4 | 11.0 | 31.3 | 56.8 | 0.9 | 0.5 | 6.7 |
| HZSM-5(27) | 33.6 | 13.9 | 7.3 | 24.5 | 64.4 | 3.7 | 0.0 | 4.3 |
| HZSM-5(150) | 33.6 | 15.0 | 7.9 | 18.4 | 73.0 | 0.7 | 0.1 | 3.0 |
| HZSM-5(300) | 33.0 | 15.0 | 8.6 | 23.2 | 67.3 | 0.9 | 1.2 | 1.7 |

$^a$O/P means the molar ratio of olefins to paraffins in $C_{2-4}$ hydrocarbons. If no special description, O/P means the same meaning in the subsequent tables.
$^b$i-$C_5$/n-$C_5$ means the molar ratio of iso-pentanes to normal-pentane. If no special description, i-$C_5$/n-$C_5$ has the same meaning in the subsequent tables.
$^c$means loading Na/$Fe_3O_4$ only and without zeolite loading.
*"Conv." means conversion and "Selec." means selectivity, if no special description, the same meaning of them in the subsequent form.

Example 2

According to the different mass ratio, weight Na/Fe$_3$O$_4$ and HZSM-5 (SiO$_2$/Al$_2$O$_3$=150), which was prepared in Example 1, and homogenously mix them to form 1 g of a granule hybrid catalyst for CO$_2$ hydrogenation reaction. Reducing conditions: 1 atm, pure H$_2$ (25 mL/min), and 350° C. for 8 h. Reaction conditions: H$_2$/CO$_2$=3.0, 320° C., 3.0 MPa, and GHSV: 4000 mL/(h·g$_{cat}$). Influences of mass ratio of Na/Fe$_3$O$_4$ to HZSM-5 on the Fe—Na/Zeolite catalyst for CO$_2$ hydrogenation has been carried out, the results (Table 2) show that, the hybrid catalyst exhibit multifunctional performances and there exists a synergistic effect between Na/Fe$_3$O$_4$ and HZSM-5. The hybrid catalyst exhibits the optimal reaction performances and the highest selectivity to gasoline-range hydrocarbons at 1 of Na—Fe$_3$O$_4$ to ZSM-5 mass ratio.

TABLE 2

Influences of the mass ratio of Na/Fe$_3$O$_4$ to HZSM-5 on the FeNa/HZSM-5(150) catalyst for CO$_2$ hydrogenation

| Fe/ZSM* (wt./wt.) | Conv. CO$_2$ (%) | Selec. CO (%) | Hydrocarbon distribution (C-mol %) | | | | O/P | i-C$_5$/n-C$_5$ |
|---|---|---|---|---|---|---|---|---|
| | | | CH$_4$ | C$_2$~C$_4$ | C$_5$~C$_{11}$ | C$_{12+}$ | | |
| 1:7 | 29.0 | 19.4 | 6.7 | 22.9 | 68.7 | 1.7 | 0.2 | 3.8 |
| 1:3 | 32.9 | 15.4 | 7.1 | 20.6 | 71.3 | 1.0 | 0.1 | 3.4 |
| 1:1 | 33.6 | 15.2 | 7.9 | 18.4 | 73.0 | 0.7 | 0.1 | 3.0 |
| 3:1 | 35.0 | 14.5 | 9.2 | 20.4 | 70.1 | 0.3 | 0.6 | 2.4 |
| 7:1 | 35.8 | 14.0 | 10.0 | 24.0 | 65.7 | 0.3 | 1.4 | 2.0 |

*"Fe/ZSM" mean "Na—Fe$_3$O$_4$/HZSM-5", if no special description, it has the same meaning in the subsequent tables.

Example 3

Weight 0.5 g Na/Fe$_3$O$_4$ and 0.5 g HZSM-5 (SiO$_2$/Al$_2$O$_3$=150), which were prepared in Example 1, respectively. Homogenously mix them to form 1 g of a granule hybrid catalyst for CO$_2$ hydrogenation reaction. Reducing conditions: 1 atm, pure H$_2$ (25 mL/min), and 350° C. for 8 h. Reaction conditions: H$_2$/CO$_2$=3.0, 280-380° C., 3.0 MPa, and GHSV: 2000 mL/(h·g$_{cat}$). Influences of reaction temperature on the Fe—Na/Zeolite catalyst for CO$_2$ hydrogenation has been carried out, the results (Table 3) show that, with increasing temperature from 280 to 380° C., conversion of CO$_2$ increases and the content of gasoline-range hydrocarbons in hydrocarbons increases before 320° C. and then decreases. The catalyst shows excellent catalytic performances for CO$_2$ hydrogenation to gasoline-range hydrocarbons at the investigated temperatures.

TABLE 3

Influences of reaction temperature on the FeNa/HZSM-5(150) catalyst for CO$_2$ hydrogenation

| Temperature (° C.) | Conv CO$_2$ (%) | Selec. CO (%) | Hydrocarbon distribution (C-mol %) | | | | O/P | i-C$_5$/n-C$_5$ |
|---|---|---|---|---|---|---|---|---|
| | | | CH$_4$ | C$_2$~C$_4$ | C$_5$~C$_{11}$ | C$_{12+}$ | | |
| 280 | 25.2 | 14.3 | 9.8 | 22.1 | 67.9 | 0.2 | 0.3 | 1.8 |
| 300 | 34.5 | 9.1 | 8.7 | 22.0 | 69.3 | 0.1 | 0.2 | 2.5 |
| 320 | 40.1 | 8.2 | 8.0 | 21.6 | 69.7 | 0.7 | 0.1 | 3.3 |
| 340 | 44.1 | 9.2 | 8.6 | 25.1 | 66.2 | 0.0 | 0.1 | 4.0 |
| 360 | 46.3 | 10.5 | 9.2 | 27.1 | 63.4 | 0.4 | 0.1 | 4.6 |
| 380 | 48.4 | 11.9 | 12.0 | 30.3 | 57.4 | 0.3 | 0.1 | 5.0 |

Example 4

Weight 0.5 g Na/Fe$_3$O$_4$ and 0.5 g HZSM-5 (SiO$_2$/Al$_2$O$_3$=150), which were prepared in Example 1, respectively. Homogenously mix them to form 1 g of a granule hybrid catalyst for CO$_2$ hydrogenation reaction. Reducing conditions: 1 atm, pure H$_2$ (25 mL/min), and 350° C. for 8 h. Reaction conditions: H$_2$/CO$_{2=3.0}$, $_{320}$° C., 1.0-5.0 MPa, and GHSV: 2000 mL/(h·g$_{cat}$). Influences of reaction pressure on the Fe—Na/Zeolite catalyst for CO$_2$ hydrogenation has been carried out, the results (Table 4) show that, with increasing pressure from 1.0 to 5.0 MPa, conversion of CO$_2$ increases and the content of gasoline-range hydrocarbons in hydrocarbons increases before 3.0 MPa and then decreases, and selectivity to CO decreases. The catalyst show excellent catalytic performances for CO$_2$ hydrogenation to gasoline-range hydrocarbons at the investigated pressures.

TABLE 4

Influences of reaction pressure on the FeNa/HZSM-5(150) catalyst for CO$_2$ hydrogenation

| P (MPa) | Conv. CO$_2$ (%) | Selec. CO (%) | Hydrocarbon distribution (C-mol %) | | | | O/P | i-C$_5$/n-C$_5$ |
|---|---|---|---|---|---|---|---|---|
| | | | CH$_4$ | C$_2$~C$_4$ | C$_5$~C$_{11}$ | C$_{12+}$ | | |
| 1.0 | 31.2 | 24.3 | 8.9 | 28.4 | 60.7 | 2.0 | 0.4 | 3.8 |
| 2.0 | 33.8 | 16.5 | 9.5 | 24.4 | 63.2 | 2.9 | 0.2 | 3.5 |
| 3.0 | 38.6 | 10.4 | 8.5 | 21.0 | 69.8 | 0.8 | 0.2 | 3.3 |
| 4.0 | 40.7 | 8.0 | 10.4 | 22.9 | 65.9 | 0.8 | 0.2 | 3.2 |
| 5.0 | 42.2 | 7.1 | 12.7 | 24.8 | 61.4 | 1.2 | 0.1 | 3.1 |

Example 5

Weight 0.5 g Na/Fe$_3$O$_4$ and 0.5 g HZSM-5 (SiO$_2$/Al$_2$O$_3$=150), which were prepared in Example 1, respectively. Homogenously mix them to form 1 g of a granule hybrid catalyst for CO$_2$ hydrogenation reaction. Reducing conditions: 1 atm, pure H$_2$ (25 mL/min), and 350° C. for 8 h. Reaction conditions: 142/CO$_{2=3.0}$, $_{320}$° C., 3.0 MPa, and GHSV: 1000-10000 mL/(h·g$_{cat}$). Influences of reaction GHSV of feedstocks on the Fe—Na/Zeolite catalyst for CO$_2$ hydrogenation has been carried out, the results (Table 5) show that, with increasing GHSV from 1000 to 10000 mL/(h·g$_{cat}$), conversion of CO$_2$ decreases and the content of gasoline-range hydrocarbons in hydrocarbons increases before 4000 mL/(h·g$_{cat}$) and then decreases. Over the hybrid catalyst, high CO$_2$ conversion (28.7%) and high content of C$_{5-11}$ hydrocarbons (63.3%) at 10000 mL/(h·g$_{cat}$) of feedstock GHSV.

TABLE 5

Influences of feedstock GHSV on the FeNa/HZSM-5(150) catalyst for CO$_2$ hydrogenation

| GHSV (mL·g$^{-1}$·h$^{-1}$) | Conv. CO$_2$ (%) | Selec. CO (%) | Hydrocarbon distribution (C-mol %) | | | | O/P | i-C$_5$/n-C$_5$ |
|---|---|---|---|---|---|---|---|---|
| | | | CH$_4$ | C$_2$~C$_4$ | C$_5$~C$_{11}$ | C$_{12+}$ | | |
| 1000 | 43.1 | 9.4 | 10.5 | 25.4 | 63.4 | 0.7 | 0.1 | 3.9 |
| 2000 | 37.2 | 11.2 | 8.3 | 21.3 | 69.7 | 0.7 | 0.1 | 3.5 |
| 4000 | 33.2 | 17.0 | 7.8 | 19.0 | 72.1 | 1.1 | 0.2 | 3.0 |
| 6000 | 31.7 | 19.0 | 8.0 | 20.2 | 70.4 | 1.5 | 0.3 | 2.7 |
| 8000 | 30.3 | 22.3 | 8.2 | 20.6 | 69.2 | 2.0 | 0.5 | 2.5 |
| 10000 | 28.7 | 25.0 | 8.4 | 21.4 | 68.0 | 2.2 | 0.7 | 2.3 |

Example 6

Weight 0.5 g Na/Fe$_3$O$_4$ and 0.5 g HZSM-5 (SiO$_2$/Al$_2$O$_3$=150), which were prepared in Example 1, respectively. Homogenously mix them to form 1 g of a granule hybrid catalyst for CO$_2$ hydrogenation reaction. Reducing conditions: 1 atm, pure H$_2$ (25 mL/min), and 350° C. for 8 h. Reaction conditions: H$_2$/CO$_2$=1.0-6.0, 320° C., 3.0 MPa, and GHSV: 2000 mL/(h·g$_{cat}$). Influences of H$_2$/CO$_2$ ratio in feedstocks on the Fe—Na/Zeolite catalyst for CO$_2$ hydrogenation has been carried out, the results (Table 6) show that, with increasing H$_2$/CO$_2$ ratio from 1.0 to 6.0, conversion of CO$_2$ evidently increases, the content of gasoline-range hydrocarbons in hydrocarbons keep high value during the investigated H$_2$/CO$_2$ ratios.

TABLE 6

Influences of feedstock H$_2$/CO$_2$ ratio on the FeNa/HZSM-5(150) catalyst for CO$_2$ hydrogenation

| Ratio H$_2$/CO$_2$ | Conv. CO$_2$ (%) | Selec. CO (%) | Hydrocarbon distribution (C-mol %) | | | | O/P | i-C$_5$/n-C$_5$ |
|---|---|---|---|---|---|---|---|---|
| | | | CH$_4$ | C$_2$~C$_4$ | C$_5$~C$_{11}$ | C$_{12+}$ | | |
| 1.0 | 22.0 | 17.6 | 4.3 | 19.5 | 75.0 | 1.2 | 0.1 | 3.4 |
| 2.0 | 27.1 | 16.5 | 6.5 | 20.3 | 72.3 | 1.0 | 0.1 | 3.4 |
| 3.0 | 36.0 | 13.1 | 8.6 | 20.8 | 70.0 | 0.7 | 0.1 | 3.4 |
| 4.0 | 45.0 | 9.7 | 10.5 | 21.3 | 68.0 | 0.2 | 0.1 | 3.4 |
| 5.0 | 53.1 | 7.4 | 11.5 | 21.4 | 66.7 | 0.4 | 0.1 | 3.4 |
| 6.0 | 59.5 | 5.7 | 12.9 | 22.2 | 64.6 | 0.3 | 0.1 | 3.4 |

Example 7

0.72 g Ga(NO$_3$)$_3$·9H$_2$O was weighted and dissolved into 7.2 mL deioned water to form solution of Ga(NO$_3$)$_3$; then 6.0 g HZSM-5 (SiO$_2$/Al$_2$O$_3$=150) was weighted and impregnated into the above solution of Ga(NO$_3$)$_3$. After stirring, stewing 12 h, drying at 60° C., calcination at 500° C. for 4 h, the Ga-modified zeolite was obtained after being ground, pelleted, and sieved. The preparation method of other metal-modified zeolites (MZSM-5) is similar as that of Ga-ZSM-5.

Weight 0.5 g Na/Fe$_3$O$_4$ prepared in Example 1 and 0.5 g 2% MZSM-5 as prepared, respectively. Homogenously mix them to form 1 g of a granule hybrid catalyst for CO$_2$ hydrogenation reaction. Reducing conditions: 1 atm, pure H$_2$ (25 mL/min), and 350° C. for 8 h. Reaction conditions: H$_2$/CO$_2$=3.0, 320° C., 3.0 MPa, and GHSV: 4000 mL/(h·g$_{cat}$). Influences of metal modification of HZSM-5 on the Fe—Na/Zeolite catalyst for CO$_2$ hydrogenation has been carried out, the results (Table 7) show that, metal modification of HZSM-5 zeolite has little influences on CO$_2$ conversion, but evidently influenced the product composition, the content of gasoline-range hydrocarbons in hydrocarbons decreases at different degrees with different metal modification.

TABLE 7

Influences of metal modification of HZSM-5 on the FeNa/HZSM-5(150) catalyst for CO$_2$ hydrogenation

| M | Conv. CO$_2$ (%) | Selec. CO (%) | Hydrocarbon distribution (C-mol %) | | | | O/P | i-C$_5$/n-C$_5$ |
|---|---|---|---|---|---|---|---|---|
| | | | CH$_4$ | C$_2$~C$_4$ | C$_5$~C$_{11}$ | C$_{12+}$ | | |
| —[a] | 33.6 | 15.2 | 7.9 | 18.4 | 73.0 | 0.7 | 0.1 | 3.0 |
| Mo | 33.6 | 16.8 | 7.9 | 18.8 | 72.4 | 0.9 | 0.1 | 2.9 |
| Cr | 35.0 | 14.3 | 8.4 | 20.5 | 70.9 | 0.2 | 0.4 | 2.5 |
| La | 35.7 | 13.8 | 8.6 | 20.7 | 70.6 | 0.1 | 0.5 | 2.3 |
| Ga | 35.6 | 14.0 | 7.9 | 20.2 | 70.1 | 1.8 | 0.1 | 3.4 |
| Zn | 35.0 | 13.9 | 8.6 | 22.8 | 68.1 | 0.4 | 1.3 | 1.8 |
| Cu | 35.9 | 13.6 | 8.1 | 24.1 | 67.7 | 0.1 | 0.2 | 3.0 |
| Co | 34.4 | 12.0 | 22.0 | 44.4 | 33.5 | 0.1 | 0.0 | 1.2 |

[a]Unmodified zeolite.

Example 8

Weight 0.5 g Na/Fe$_3$O$_4$ and 0.5 g HZSM-5 (SiO$_2$/Al$_2$O$_3$=150), which were prepared in Example 1, respectively. Na/Fe$_3$O$_4$ and HZSM-5 were packed into the reactor according to the sequences of iron-based catalyst layer, and zeolite layer, among which iron-based catalyst layer is near to the feedstock inlet, there is an isolated layer composed of inert quartz sands between iron-based catalyst layer and zeolite layer. Then the reactor with hybrid catalyst form was carried out the catalytic stability test of CO$_2$ hydrogenation reaction. Reducing conditions: 1 atm, pure H$_2$ (25 mL/min), and 350° C. for 8 h. Reaction conditions: H$_2$/CO$_2$=3.0, 320° C., 3.0 MPa, and GHSV: 4000 mL/(h·g$_{cat}$). The results (Table 8) show that, the loading hybrid catalyst exhibit excellent performances of CO$_2$ hydrogenation during 1000 h reaction, there is no evident deactivation found for this hybrid catalyst. The composition analysis (Table 9) of gasoline products show that gasoline-range hydrocarbons are mainly composed of isoparaffins and aromatics, the content of olefins in gasoline is low, the composition of gasoline products meet the requirement of standard China-V gasoline.

TABLE 8

1000 h catalytic stability test results of FeNa/HZSM-5(150) catalyst with multilayer catalyst packing method for CO$_2$ hydrogenation

| Time on Stream (h) | Conv. CO$_2$ (%) | Selec. CO (%) | Hydrocarbon distribution (C-mol %) | | | | O/P | i-C$_5$/ n-C$_5$ |
|---|---|---|---|---|---|---|---|---|
| | | | CH$_4$ | C$_2$~C$_4$ | C$_5$~C$_{11}$ | C$_{12+}$ | | |
| 4 | 33.2 | 14.6 | 9.3 | 24.0 | 66.2 | 0.5 | 0.1 | 3.3 |
| 100 | 32.2 | 14.9 | 8.8 | 22.4 | 67.7 | 1.1 | 0.1 | 3.1 |
| 200 | 29.6 | 17.5 | 8.8 | 21.9 | 67.6 | 1.6 | 0.1 | 3.1 |
| 300 | 28.1 | 18.1 | 9.6 | 23.0 | 66.4 | 1.1 | 0.1 | 3.2 |
| 400 | 27.4 | 19.0 | 9.7 | 23.2 | 65.9 | 1.2 | 0.1 | 3.2 |
| 500 | 27.5 | 18.7 | 10.0 | 23.7 | 65.3 | 1.0 | 0.2 | 3.2 |
| 600 | 27.0 | 19.2 | 10.1 | 24.4 | 65.0 | 0.5 | 0.2 | 3.1 |
| 700 | 27.3 | 18.9 | 10.1 | 24.1 | 65.1 | 0.7 | 0.2 | 3.1 |
| 800 | 26.8 | 19.6 | 10.1 | 24.2 | 64.9 | 0.8 | 0.2 | 3.1 |
| 900 | 26.7 | 19.9 | 10.1 | 24.5 | 64.5 | 0.8 | 0.2 | 3.1 |
| 1000 | 26.8 | 19.8 | 10.2 | 24.6 | 64.3 | 0.9 | 0.2 | 3.1 |

TABLE 9

Composition of gasoline product at reaction 1000 h

| Gasoline-range hydrocarbons | Content (C-mol %) |
|---|---|
| Normal paraffins | 8.0 |
| Olefins | 5.4 |
| Isoparaffins | 44.0 |
| Cyclanes | 12.6 |
| Aromatics | 30.0 |

For this invention of CO$_2$ hydrogenation to gasoline, the single-pass conversion of CO$_2$ could achieve more than 33%, in hydrocarbon products, selectivity to methane is lower than 8%, selectivity to C$_{5-11}$ gasoline-range hydrocarbons is higher than 70%, and the gasoline products with high octane-number were mainly composed of isoparaffins and aromatics. A new route for gasoline production from carbon dioxide was invented in this application.

The invention claimed is:

1. A method for direct production of gasoline-range hydrocarbons via carbon dioxide hydrogenation comprising: converting a gas stream comprising carbon dioxide and hydrogen to gasoline-range hydrocarbons in the presence of a multifunctional catalyst, wherein the multifunctional catalyst comprises an iron-based catalyst for carbon dioxide hydrogenation as a first component and at least one or two kinds of zeolites optionally modified with a metal as a second component, the mass ratio of the first component to the second component is 1:10 to 10:1, and the first and second components are mixed according to any one of the following three methods:
   (1) powder mixing method comprising: grinding and mixing powders of iron-based catalyst and zeolite at the required mass ratio of iron-catalyst to zeolite; pelleting, crushing, and sieving to form the multifunctional catalyst;
   (2) granule mixing method comprising: pelleting iron-based catalyst powders and zeolite powders, crushing, and sieving; mixing homogeneously the sieved granules of iron-based catalysts and zeolites at the required mass ratio of iron-catalyst to zeolite to form the multifunctional catalyst;
   (3) multilayer catalyst packing method comprising: packing catalyst into a reactor according to the sequences of an iron-based catalyst layer and a zeolite layer, wherein the iron-based catalyst layer is near to the feedstock inlet and the zeolite layer is far to the feedstock inlet; wherein between the iron-based catalyst layer and the zeolite layer, there is an optional isolating layer composed of inert materials; and wherein the mass ratio of the isolating layer to multifunctional catalyst is 0.01-10.

2. The method according to claim 1, wherein the converting is conducted under the following conditions: a temperature of 250-450° C., a pressure of 0.01-10.0 MPa, a gas hour space velocity of the gas stream being 500-50000 ml/((h·g$_{cat}$), and a molar ratio of hydrogen to carbon dioxide in the gas stream being 0.5-8.0.

3. The method according to claim 1, wherein the iron-based catalyst for carbon dioxide hydrogenation comprises Fe$_3$O$_4$ as a main active component, and optionally, no more than 30% by weight, an oxide promoter selected from the group consisting of sodium oxide, potassium oxide, manganese oxides, copper oxide, zirconium oxide, vanadium oxides, zinc oxide, cerium oxide, and combinations thereof.

4. The method according to claim 1, wherein the zeolites are selected from the group consisting of ZSM-5, ZSM-22, ZSM-23, Y, Beta, MOR, MCM-22, and combinations thereof, and the metal is selected from the group consisting of Mo, Zn, Rh, Ru, Ga, Cr, Co, Ni, Na, Cu, Pd, Pt, La, and combinations thereof in the amount of 0.1%-20%.

5. The method according to claim 1 comprising:
making the iron-based catalyst component for $CO_2$ hydrogenation by one of the following three preparation methods:

A. one-pot synthesis method, comprising the following steps:
(1) mixing and dissolving a soluble Fe (II) salt and a soluble Fe (III) salt to form a salt solution-I; or mixing and dissolving the soluble Fe (II) salt, the Fe (III) salt, and a soluble promoter salt to form a salt solution-II; wherein in the salt solution-I or salt solution-II, the concentration of Fe (III) is 0.05-1 mol/L, and adding a HCl solution with 5-12.1 mol/L HCl concentration into the salt solution-I or solution-II to adjust the pH value to 0-3, the molar ratio of Fe(III) to Fe(II) in the salt solutions-I and II is 2:(1-3);
wherein the soluble Fe (II) salt and Fe (III) salt are salt compounds that are dissolvable in water; and the soluble promoter salt is a salt compound that is dissolvable in water;
(2) adding dropwise an alkali solution into the salt solution I or salt solution II obtained from step (1) for titration to adjust the pH from 0-3 to 9-12; and aging the solution for 1-5 hours after finishing the titration; wherein the alkali solution is an alkaline solution that is capable of adjusting the pH value of the salt solution I or salt solution II; the concentration of the alkali solution is 0.1-10 mol/L;
(3) separating precipitates from the solution obtained in step (2) by magnetic adsorption, centrifugation or suction filtration, and then fully washing the precipitates with distilled water, drying, and optionally calcining at 200-600° C. for 2-10 hours to obtain the iron-based catalyst;

B. one-pot synthesis method, comprising the following steps:
(1) mixing and dissolving a soluble Fe(II) salt and a soluble Fe(III) salt to form a salt solution, wherein in the salt solution, the concentration of Fe(III) is 0.05-1 mol/L, and adding a HCl solution with 5-12.1 mol/L HCl concentration into the salt solution to adjust the pH value to 0-3; the molar ratio of Fe(III) to Fe(II) in the salt solution is 2:(1-3);
(2) adding dropwise the alkali solution described in method A is added dropwise into the salt solution obtained from step (1) for titration to adjust pH value of the salt solution from 0-3 to 9-12; and aging the titrated solution is aged for 1-5 hours;
(3) after reaction in (2), separating precipitates from the solution obtained in (2) by magnetic adsorption, centrifugation or suction filtration; fully washing the precipitates with distilled water, wherein the content of residue Na or K is controlled by controlling the times and water usage for washing; and drying the washed precipitates, optionally calcining at 200-600° C. for 2-10 hours to obtain the iron-based catalyst with promoter Na or K;

C. first synthesis of $Fe_3O_4$ by coprecipitation, and then addition of promoter by impregnation:
(1) mixing and dissolving a soluble Fe(II) salt and a Fe(III) salt to form a salt solution, wherein in the salt solution, the concentration of Fe(III) is 0.05-1 mol/L, adding a HCl solution with 5-12.1 mol/L HCl concentration into the salt solution to adjust the pH value to 0-3; the molar ratio of Fe(III) to Fe(II) in the salt solution is 2:(1-3);
(2) adding dropwise the alkali solution described in method A into the salt solution obtained from step (1) for titration to adjust pH value of the salt solution from 0-3 to 9-12; aging the salt solution for 1-5 hours after finishing the titration;
(3) after reaction in (2), separating precipitates from the salt solutions by magnetic adsorption, centrifugation or suction filtration, and fully washing the precipitates with distilled water, and drying to form active composition $Fe_3O_4$;
(4) catalyst synthesis from combination of active composition $Fe_3O_4$ and promoter salt by impregnation via a procedure as described below: calculating the mass of promoter salt to determine the needed promoter content, and preparing a solution of a promoter salt, impregnating $Fe_3O_4$ as prepared with the promoter salt solution by equivalent-volume impregnation, and stirring, stewing, drying, and calcinating at 200-600° C. for 2-10 h to obtain the iron-based catalyst.

6. The method according to claim 1, wherein the zeolite modification is carried out according to one of the following methods for supporting the metal component:
(1) equivalent-volume impregnation method comprising: calculating the theoretical mass of metal salt to determine the needed amount of the metal content; preparing the solution of metal salt; wherein the metal salt is one, two or more of the following salts: nitrate, chloride, bromide, acetate, acetylacetonate, citrate, and oxalate; impregnating the zeolite to be modified with the as-prepared salt solution by equivalent-volume impregnation, and stirring, stewing, drying, and calcinating at 300-700° C. for 2-10 h to obtain the modified zeolite;
(2) ion-exchanged method comprising: calculating the theoretical mass of metal salt to determine the needed amount of the metal content, preparing the solution of metal salt; the metal salt is one, two or more of the following salts: nitrate, chloride, bromide, acetate, acetylacetonate, citrate, and oxalate; mixing the zeolite to be modified with the as-prepared metal salt solution at 1:(10-200) of mass ratio of solid to solution, and ion-exchanging for 2-24 h; and water washing, drying, calcining at 300-700° C. for 2-10 h to obtain the metal-modified zeolite.

7. The method according to claim 1, wherein the gas stream comprises a gas containing carbon dioxide that is selected from the group consisting of industrial waste gas, automobile exhaust, coal combustion exhaust, carbon dioxide in atmosphere or seawater, and combinations thereof.

8. The method according to claim 1 wherein the mass ratio of the first component to the second component is 1:3 to 3:1.

9. The method according to claim 3 wherein the iron-based catalyst comprises 0.5-10% by weight of the oxide promoter.

10. The method according to claim 4 wherein the zeolites are one or more of ZSM-5 with 20-350 molar ratio of $SiO_2$ to $Al_2O_3$, and MCM-22 with 20-200 molar ratio of $SiO_2$ to $Al_2O_3$.

11. The method according to claim 4 wherein the zeolites comprise 0.5%-10% by weight of the metal.

12. The method according to claim 5 wherein the soluble Fe (II) salt and Fe (III) salt compounds are selected from the group consisting of chlorides, nitrates, acetates, and combinations thereof.

13. The method according to claim 5 wherein the soluble promoter salt is a salt selected from the group consisting of chlorides, nitrates, acetates, and combinations thereof.

14. The method according to claim 5 wherein the alkali solution is selected from the group consisting of solutions of NaOH, KOH, $Na_2CO_3$, $NaHCO_3$, $K_2CO_3$, $KHCO_3$, $Na_2C_2O_4$, $K_2C_2O_4$, RCOONa, RCOOK, $NH_3.H_2O$, and combinations thereof.

15. The method according to claim 14 wherein in RCOOK and RCOONa, R is a methyl, ethyl, or phenyl group.

16. The method according to claim 1, wherein the two components of multifunctional catalysts are mixed by granule mixing or multilayer catalyst packing.

17. A method for direct production of gasoline-range hydrocarbons via carbon dioxide hydrogenation comprising:
   a) making a multifunctional catalyst comprising an iron-based catalyst for carbon dioxide hydrogenation as a first component and at least one or two kinds of zeolites optionally modified with a metal as a second component, wherein the mass ratio of the first component to the second component is 1:10 to 10:1, and the iron-based catalyst for carbon dioxide hydrogenation comprises $Fe_3O_4$ as a main active component;
   b) loading the multifunctional catalyst prepared in step a) into a reactor; and
   c) feeding a gas stream comprising carbon dioxide and hydrogen into the reactor loaded with the multifunctional catalyst in step b) to convert the gas stream into the gasoline-range.

18. The method of claim 17 wherein the iron-based catalyst for carbon dioxide hydrogenation comprises $Na/Fe_3O_4$, and the second component is HZSM-5.

* * * * *